US012115204B2

(12) United States Patent
Gu et al.

(10) Patent No.: US 12,115,204 B2
(45) Date of Patent: Oct. 15, 2024

(54) COMPOUND PREPARATION FOR NEURANAGENESIS, AND PREPARATION METHOD THEREFOR AND USE THEREOF

(71) Applicant: NANTONG UNIVERSITY, Nantong (CN)

(72) Inventors: Xiaosong Gu, Nantong (CN); Chunkang Tang, Nantong (CN); Fei Ding, Nantong (CN); Xiaoming Yang, Nantong (CN); Qiong Cheng, Nantong (CN); Hualin Sun, Nantong (CN); Lai Xu, Nantong (CN)

(73) Assignee: NANTONG UNIVERSITY, Nantong (CN)

( * ) Notice: Subject to any disclaimer, the term of this patent is extended or adjusted under 35 U.S.C. 154(b) by 0 days.

(21) Appl. No.: 17/790,646

(22) PCT Filed: Jan. 5, 2021

(86) PCT No.: PCT/CN2021/070266
§ 371 (c)(1),
(2) Date: Jul. 1, 2022

(87) PCT Pub. No.: WO2022/016827
PCT Pub. Date: Jan. 27, 2022

(65) Prior Publication Data
US 2023/0043437 A1    Feb. 9, 2023

(30) Foreign Application Priority Data
Jul. 20, 2020 (CN) .......... 202010697245.X

(51) Int. Cl.
| | |
|---|---|
| *A61K 36/481* | (2006.01) |
| *A61K 35/583* | (2015.01) |
| *A61K 36/076* | (2006.01) |
| *A61K 36/21* | (2006.01) |
| *A61K 36/232* | (2006.01) |
| *A61K 36/284* | (2006.01) |
| *A61K 36/286* | (2006.01) |
| *A61K 36/64* | (2006.01) |
| *A61K 36/725* | (2006.01) |
| *A61K 36/815* | (2006.01) |

(52) U.S. Cl.
CPC .......... *A61K 36/481* (2013.01); *A61K 35/583* (2013.01); *A61K 36/076* (2013.01); *A61K 36/21* (2013.01); *A61K 36/232* (2013.01); *A61K 36/284* (2013.01); *A61K 36/286* (2013.01); *A61K 36/64* (2013.01); *A61K 36/725* (2013.01); *A61K 36/815* (2013.01); *A61K 2236/13* (2013.01); *A61K 2236/331* (2013.01); *A61K 2236/51* (2013.01)

(58) Field of Classification Search
None
See application file for complete search history.

(56) References Cited

U.S. PATENT DOCUMENTS

2017/0368122 A1* 12/2017 Choi .................. A61P 25/28

FOREIGN PATENT DOCUMENTS

| | | |
|---|---|---|
| CN | 1263768 A | 8/2000 |
| CN | 1485077 A | 3/2004 |
| CN | 101254282 A * | 9/2008 |
| CN | 102091166 A | 6/2011 |
| CN | 102836274 A * | 12/2012 |
| CN | 103705897 A * | 4/2014 |
| CN | 103877185 A * | 6/2014 |
| CN | 104324355 A | 2/2015 |
| CN | 104758404 A | 7/2015 |
| CN | 105079515 A | 11/2015 |
| CN | 106237010 A | 12/2016 |
| CN | 106266408 A | 1/2017 |
| CN | 106310120 A | 1/2017 |
| CN | 111759915 A | 10/2020 |
| EA | 200101077 A1 | 4/2002 |
| JP | H6-107556 A | 4/1994 |
| JP | 2007-230938 A | 9/2007 |
| JP | 2013-209354 A | 10/2013 |
| KR | 2003-0020585 A | 3/2003 |
| RU | 2011139190 A | 5/2013 |

(Continued)

OTHER PUBLICATIONS

Abstract, Lu, T., et al., [The research on analgestic and anti-inflammatory action of different processed products of Achyranthes bidentata], Journal of Chinese Medicinal Materials, Oct. 1, 1997, 20(10):507-509 (Year: 1997).*
Machine translation, CN 103705897 A.*
Rui, C., et al., Protective effects of Lycium barbarum polysaccharide on neonatal rat primary cultured hippocampal neurons injured by oxygen-glucose deprivation and reperfusion, J Mol Histol. Oct. 2012;43(5):535-42 (Year: 2012).*
Liu, Z., et al., Jujuboside A, a neuroprotective agent from semen Ziziphi Spinosae ameliorates behavioral disorders of the dementia mouse model induced by Aβ1-42, European Journal of Pharmacology vol. 738 (Sep. 2014) 206-213 (Year: 2014).*
Machine translation of CN 103877185A.*
Machine translation of CN 101254282A.*

(Continued)

Primary Examiner — H. Sarah Park
(74) Attorney, Agent, or Firm — HAUPTMAN HAM, LLP

(57) ABSTRACT

Disclosed are a compound preparation for neuranagenesis, and a preparation method therefor and the use thereof. The compound preparation for neuranagenesis comprises the raw medicinal materials in parts by weight: 10-20 parts of raw *Astragali radix*, 10-20 parts of Rehmaimiae *Radix praeparata*, 10-20 parts of *Actyranthes bidentata*, 6-15 parts of *Jujubae fructus*, 6-15 parts of *Lycii fructus*, 6-15 parts of parched *Ziziphi spinosae* semen, 6-12 parts of *Angelicae smensis radix*, 3-9 parts of *Carthami flos*, 6-15 parts of *Poria*, 6-15 parts of parched *Atractylodis macrocephalae rhizoma* and 10-20 parts of *Zaocys*. The compound preparation can be used for preparing drugs to treat nerve damage diseases, and can be prepared into oral liquids, granules, dissolved granules and tablets.

7 Claims, No Drawings

(56) References Cited

FOREIGN PATENT DOCUMENTS

RU          2017123242 A     1/2019

OTHER PUBLICATIONS

International Search Report and Written Opinion issued in International Application No. PCT/CN2021/070266; mailed Apr. 26, 2021; 12 pgs.
Mingming, Zhou, et al; Studies on the Pharmacological Action of Nerve Growth Decotion on Promoting Blood Circulation and Stamina of Mice; The key Lab neuroregeration of Jiangsu Province, Nantong Medical College, Nantong 226001; Apr. 17, 2003; pp. 369-370.
Lu, Ming-Chin et al; Effect of Astragalus membranaceus in Rats on Peripheral Nerve Regeneration: in Vitro and In Vivo Studies; The Journal of TRAUMA Injury, Infection, and Critical Care; vol. 68, No. 2, Feb. 2010; 7 pgs.

* cited by examiner

COMPOUND PREPARATION FOR NEURANAGENESIS, AND PREPARATION METHOD THEREFOR AND USE THEREOF

RELATED APPLICATIONS

The present application is a U.S. National Phase of International Application Number PCT/CN2021/070266 filed Jan. 5, 2021, and claims priority to Chinese Application Number 202010697245.X filed Jul. 20, 2020.

TECHNICAL FIELD

The present invention belongs to the technical field of traditional Chinese medicine preparations, and particularly relates to a compound preparation for neuranagenesis, and a preparation method therefor and use thereof.

BACKGROUND

Nerve injuries may cause partial or total loss of motor and sensory functions and lead to a high disability rate, with clinical manifestations of flaccid tendons and vessels, myasthenia, skin numbness, body weakness, limb numbness and even paralysis, belonging to "flaccidity syndrome", "arthromyodynia" and the like according to the dialectics of traditional Chinese medicine. Due to the nerve injuries caused by accidents related to modern traffic, work accidents, earthquake disasters, wars, tumor operations, etc., the incidence of nerve injuries is increasing year by year, which severely affects the living quality of the patients and brings heavy financial and social burdens to the society and their families. For more than a century, how to promote the restoration and regeneration of the damaged nerves has always been a major challenge and a hot topic in the fields of pharmacy, neuroscience and medicine.

At present, few drugs are clinically available for nerve injuries. Treatment of central nerve injuries using a nerve growth factor (NGF) has a certain efficacy. However, since the NGF is extracted from a culture solution of brain glioma cells, clinical trials of NGF have a potential risk of inducing tumors. For peripheral nerve injuries, vitamin B6 is adopted clinically, and mecobalamin (Methycobal) is a vitamin derivative and has a certain efficacy. Clinical practices in decades indicate that a drug treatment mode of "one drug for one target for one disease" has a great limitation, and provides poor clinical efficacy.

Therefore, it is an expectation of the majority of patients, a major demand of the society and a need of innovations in human neuroscience, pharmacy and medicine to research and develop a safe and effective traditional Chinese medicine for promoting neuranagenesis.

How to solve the above-mentioned technical problem is the topic of the present invention.

SUMMARY

An objective of the present invention is to provide a compound preparation for neuranagenesis, and a preparation method therefor and use thereof to address the above-mentioned problem, where the compound preparation has obvious effects of promoting nerve growth, promoting myelination of the regenerated nerves, promoting reinnervation of the denervated target muscles and providing protection after nerve injuries, thereby providing a scientific basis for the effect of traditional Chinese medicine in promoting neuranagenesis after injuries, and laying a firm foundation for clinical application of the prescription.

In order to achieve the above-mentioned objective of the present invention, the present invention adopts the following technical solution: a compound preparation for neuranagenesis, where the compound preparation comprises the raw medicinal materials in parts by weight: 10-20 parts of raw *Astragali radix*, 10-20 parts of Rehmaimiae *Radix praeparata*, 10-20 parts of *Actyranthes bidentata*, 6-15 parts of *Jujubae fructus*, 6-15 parts of *Lycii fructus*, 6-15 parts of parched *Ziziphi spinosae* semen, 6-12 parts of *Angelicae smensis radix*, 3-9 parts of *Carthami flos*, 6-15 parts of *Poria*, 6-15 parts of parched *Atractylodis macrocephalae rhizoma* and 10-20 parts of *Zaocys*.

Further, the compound preparation comprises the raw medicinal materials in parts by weight: 15 parts of raw *Astragali radix*, 15 parts of Rehmaimiae *Radix praeparata*, 15 parts of *Actyranthes bidentata*, 10 parts of *Jujubae fructus*, 10 parts of *Lycii fructus*, 10 parts of parched *Ziziphi spinosae* semen, 6 parts of *Angelicae smensis radix*, 3 parts of *Carthami flos*, 10 parts of *Poria*, 10 parts of parched *Atractylodis macrocephalae rhizoma* and 15 parts of *Zaocys*.

Further, the compound preparation also comprises an effective dose of the formulation components of the compound preparation and pharmaceutically acceptable excipients.

Further, the dosage form of the compound preparation for neuranagenesis comprises oral liquids, granules, dissolved granules and tablets.

In order to better achieve the above-mentioned objective of the present invention, the present invention also provides a method for preparing a compound preparation for neuranagenesis, where when the dosage form of the compound preparation is oral liquid, the preparation method comprises the following steps:

(1) preparing raw materials in parts by weight: 15 parts of raw *Astragali radix*, 10 parts of *Jujubae fructus*, 15 parts of Rehmaimiae *Radix praeparata*, 10 parts of *Lycii fructus*, 15 parts of *Actyranthes bidentata*, 10 parts of parched *Ziziphi spinosae* semen, 6 parts of *Angelicae smensis radix*, 3 parts of *Carthami flos*, 10 parts of *Poria*, 10 parts of parched *Atractylodis macrocephalae rhizoma* and 15 parts of *Zaocys*, and rinsing the medicinal materials with water to remove impurities;

(2) soaking the raw materials in deionized water at 25° C. for 120 min;

(3) performing water extraction, and decocting at 100° C. for 20 min;

(4) taking the decoction and allowing same to stand at 4° C. for 12 h under sterile conditions, performing filtration and concentration, and adding benzoic acid or sodium benzoate; and (5) performing filling and sterilization to obtain the oral liquid.

In order to better achieve the above-mentioned objective of the present invention, the present invention also provides a method for preparing a compound preparation with a dosage form of granules, where the preparation method comprises the following steps:

(1) preparing raw materials in parts by weight: 15 parts of raw *Astragali radix*, 10 parts of *Jujubae fructus*, 15 parts of Rehmaimiae *Radix praeparata*, 10 parts of *Lycii fructus*, 15 parts of *Actyranthes bidentata*, 10 parts of parched *Ziziphi spinosae* semen, 6 parts of *Angelicae smensis radix*, 3 parts of *Carthami flos*, 10 parts of *Poria*, 10 parts of parched *Atractylodis mac-* rocephalae rhizoma and 15 parts of *Zaocys*, and rinsing the medicinal materials with water to remove impurities;
(2) soaking the raw materials in deionized water at 25° C. for 120 min;
(3) performing water extraction, and decocting at 100° C. for 20 min;
(4) taking the decoction and allowing same to stand at 4° C. for 12 h under sterile conditions, performing filtration and concentration, and adding benzoic acid or sodium benzoate; and
(5) performing drying, granulation, filling and sterilization to obtain the granules.

Further, use of the compound preparation for neuranagenesis in drugs for treating nerve damage diseases.

Further, the monarch drugs of the compound preparation: raw *Astragali radix*, Rehmaimiae *Radix praeparata*, *Actyranthes bidentata*, *Jujubae fructus*, *Lycii fructus* and parched *Ziziphi spinosae* semen; ministerial drugs: *Angelicae smensis radix* and *Carthami flos*; adjuvants: *Poria* and parched *Atractylodis macrocephalae rhizoma*; and conductant drug: *Zaocys*.

Further, the compound preparation has the functions of tonifying qi and replenishing blood, tonifying five internal organs, promoting nerve growth, promoting myelination, and clearing and activating the channels and collaterals, and is suitable for the conditions after nerve injuries of deficiency of qi and blood, disharmony in channels and collaterals, myasthenia, skin numbness and acral weakness.

Compared with the prior art, the present invention has the following beneficial effects:
(1) The compound preparation for neuranagenesis provided by the present invention has the advantages of low toxicity and safety as well as unique advantages of "coordination of multiple active ingredients, multiple levels and multiple targets and overall comprehensive effects", and accordingly, we have shaped the characteristics of the pharmaceutical formulation of traditional Chinese medicine on the basis of traditional experiential prescriptions and with reference to the requirements of modern neuranagenesis theories.
(2) Innovations in the effects of the drugs of the prescription are targeted at main pathological mechanisms after nerve injuries: deficiency of healthy qi, deficiency of qi and blood, deficiency of liver and kidney and deficiency of five internal organs. A theory of traditional Chinese medicine, "treating deficiency with tonification", adopts a prescription combining *Radix* astragah for tonifying middle-Jiao and qi, *Jujubae fructus* for tonifying qi and nourishing kidney and tonifying liver and soothing nerves, Rehmaimiae *Radix praeparata* for nourishing yin and supplementing blood and tonifying essence and supplementing bone marrow, *Lycii fructus* for tonifying liver and improving eyesight and nourishing kidney and moistening lung, *Achyranthes bidentata* for supplementing bone marrow and essence, parched *Ziziphi spinosae* semen, etc., which has reliable effects of tonifying qi, blood, yin and yang and replenishing deficiency of five internal organs.
(3) Nerve injuries cause limb paralysis, blocked blood flow and impeded qi and blood; and with respect to blood stasis and qi stagnation, the prescription adopts *Angelicae smensis radix* and *Carthami flos*. With *Poria* for promoting urination, tonifying spleen and harmonizing stomach, the parched *Atractylodis macrocephalae rhizoma* for tonifying spleen and nourishing stomach and eliminating dampness and harmonizing the middle-Jiao, and *Zaocys* for dispelling wind evil and clearing and activating the channels and collaterals, the prescription facilitates functional recovery after nerve injuries.
(4) A series of pharmacological studies on the prescription discover that the prescription has obvious effects of promoting nerve growth, promoting myelination of the regenerated nerves, promoting myelination of the denervated target muscles and providing protection after nerve injuries, thereby providing a scientific basis for traditional Chinese medicine that promotes neuranagenesis after injuries, and laying a firm foundation for clinical application of the prescription.

DETAILED DESCRIPTION OF THE EMBODIMENTS

The compound preparation for neuranagenesis provided by the present invention has obvious effects of promoting nerve growth, promoting myelination of the regenerated nerves, promoting myelination of the denervated target muscles and providing protection after nerve injuries, thereby providing a scientific basis for traditional Chinese medicine that promotes neuranagenesis after injuries, and laying a firm foundation for clinical application of the prescription.

The present invention adopts the following technical solution: a compound preparation for neuranagenesis, where the compound preparation includes the raw medicinal materials in parts by weight: 10-20 parts of raw *Astragali radix*, 10-20 parts of Rehmaimiae *Radix praeparata*, 10-20 parts of *Actyranthes bidentata*, 6-15 parts of *Jujubae fructus*, 6-15 parts of *Lycii fructus*, 6-15 parts of parched *Ziziphi spinosae* semen, 6-12 parts of *Angelicae smensis radix*, 3-9 parts of *Carthami flos*, 6-15 parts of *Poria*, 6-15 parts of parched *Atractylodis macrocephalae rhizoma* and 10-20 parts of *Zaocys*.

Specifically, the compound preparation includes the raw medicinal materials in parts by weight: 15 parts of raw *Astragali radix*, 15 parts of Rehmaimiae *Radix praeparata*, 15 parts of *Actyranthes bidentata*, 10 parts of *Jujubae fructus*, 10 parts of *Lycii fructus*, 10 parts of parched *Ziziphi spinosae* semen, 6 parts of *Angelicae smensis radix*, 3 parts of *Carthami flos*, 10 parts of *Poria*, 10 parts of parched *Atractylodis macrocephalae rhizoma* and 15 parts of *Zaocys*.

Specifically, the compound preparation also includes an effective dose of the formulation components of the compound preparation and pharmaceutically acceptable excipients.

Specifically, the dosage form of the compound preparation for neuranagenesis includes oral liquids, granules, dissolved granules and tablets.

In order to better achieve the objective of the present invention, the present invention also provides a method for preparing a compound preparation for neuranagenesis, where when the dosage form of the compound preparation is oral liquid, the preparation method includes the following steps:
(1) preparing raw materials in parts by weight: 15 parts of raw *Astragali radix*, 10 parts of *Jujubae fructus*, 15 parts of Rehmaimiae *Radix praeparata*, 10 parts of *Lycii fructus*, 15 parts of *Actyranthes bidentata*, 10 parts of parched *Ziziphi spinosae* semen, 6 parts of *Angelicae smensis radix*, 3 parts of *Carthami flos*, 10 parts of *Poria*, 10 parts of parched *Atractylodis mac-* rocephalae rhizoma and 15 parts of Zaocys, and rinsing the medicinal materials with water to remove impurities;
(2) soaking the raw materials in deionized water at 25° C. for 120 min;
(3) performing water extraction, and decocting at 100° C. for 20 min;
(4) taking the decoction and allowing same to stand at 4° C. for 12 h under sterile conditions, performing filtration and concentration, and adding benzoic acid or sodium benzoate; and
(5) performing filling and sterilization to obtain the oral liquid.

In order to better achieve the objective of the present invention, the present invention also provides a method for preparing a compound preparation with a dosage form of granules, where the preparation method includes the following steps:
(1) preparing raw materials in parts by weight: 15 parts of raw Astragali radix, 10 parts of Jujubae fructus, 15 parts of Rehmaimiae Radix praeparata, 10 parts of Lycii fructus, 15 parts of Actyranthes bidentata, 10 parts of parched Ziziphi spinosae semen, 6 parts of Angelicae smensis radix, 3 parts of Carthami flos, 10 parts of Poria, 10 parts of parched Atractylodis macrocephalae rhizoma and 15 parts of Zaocys, and rinsing the medicinal materials with water to remove impurities;
(2) soaking the raw materials in deionized water at 25° C. for 120 min;
(3) performing water extraction, and decocting at 100° C. for 20 min;
(4) taking the decoction and allowing same to stand at 4° C. for 12 h under sterile conditions, performing filtration and concentration, and adding benzoic acid or sodium benzoate; and
(5) performing drying, granulation, filling and sterilization to obtain the granules.

Specifically, use of the compound preparation for neuranagenesis in drugs for treating nerve damage diseases.

Specifically, the monarch drugs of the compound preparation: raw Astragali radix, Rehmaimiae Radix praeparata, Actyranthes bidentata, Jujubae fructus, Lycii fructus and parched Ziziphi spinosae semen; ministerial drugs: Angelicae smensis radix and Carthami flos; adjuvants: Poria and parched Atractylodis macrocephalae rhizoma; and conductant drug: Zaocys.

Specifically, the compound preparation has the functions of tonifying qi and replenishing blood, tonifying five internal organs, promoting nerve growth, promoting myelination, and clearing and activating the channels and collaterals, and is suitable for the conditions after nerve injuries of deficiency of qi and blood, disharmony in channels and collaterals, myasthenia, skin numbness and acral weakness.

Example 1: The Compound Preparation for Neuranagenesis with a Dosage Form of Oral Liquid A process of preparing the oral liquid of the present invention was: 150 parts of raw Astragali radix, 150 parts of Rehmaimiae Radix praeparata, 150 parts of Actyranthes bidentata, 100 parts of Jujubae fructus, 100 parts of Lycii fructus, 100 parts of parched Ziziphi spinosae semen, 60 parts of Angelicae smensis radix, 30 parts of Carthami flos, 100 parts of Poria, 100 parts of parched Atractylodis macrocephalae rhizoma and 150 parts of Zaocys were taken.

A preparation method therefor included the following steps:
(1) the medicinal materials in parts by weight were rinsed with water to remove impurities;
(2) the medicinal materials were prepared into 1,190 parts by volume, and soaked in deionized water at 25° C. for 120 min;
(3) water extraction was performed, and decocting was performed at 100° C. for 20 min;
(4) the decoction was taken and allowed to stand at 4° C. for 12 h under sterile conditions, filtration and concentration were performed, and benzoic acid or sodium benzoate was added; and
(5) filling and sterilization were performed to obtain an oral liquid preparation.

Example 2: The Compound Preparation for Neuranagenesis with a Dosage Form of Granules A process of preparing the oral liquid of the present invention was: 150 parts of raw Astragali radix, 150 parts of Rehmaimiae Radix praeparata, 150 parts of Actyranthes bidentata, 100 parts of Jujubae fructus, 100 parts of Lycii fructus, 100 parts of parched Ziziphi spinosae semen, 60 parts of Angelicae smensis radix, 30 parts of Carthami flos, 100 parts of Poria, 100 parts of parched Atractylodis macrocephalae rhizoma and 150 parts of Zaocys were taken.

A preparation method therefor included the following steps:
(1) the medicinal materials were rinsed with water to remove impurities;
(2) the medicinal materials were prepared into 1,190 parts by volume, and soaked in deionized water at 25° C. for 120 min;
(3) water extraction was performed, and decocting was performed at 100° C. for 20 min;
(4) the decoction was taken and allowed to stand at 4° C. for 12 h under sterile conditions, filtration and concentration were performed, and benzoic acid or sodium benzoate was added; and
(5) drying, granulation, filling and sterilization were performed to obtain granules.

Example 3: Experimental Study on the Compound Preparation for Neuranagenesis in Promoting Regeneration of Sciatic Nerves in Rats Materials and methods: 50 SD rats were randomly divided into 5 groups, where low-dose, medium-dose and high-dose groups of the oral liquid of the compound preparation for neuranagenesis were administered with crude drugs at a dose of 0.9 g/kg, 1.8 g/kg and 3.6 g/kg respectively, a Mecobalamin group was administered at a dose of 625 μg/kg, and a control group was given with double distilled water at an equivalent volume.

A rat sciatic nerve injury model was established by referring to the paper and method published by Smith G M et al., and SFI (sciatic functional index) determination, histological examination and statistical treatment of data were performed.

Results: the traditional Chinese medicine group and the Mecobalamin group were obviously superior to the blank control group in terms of SFI, and statistical analysis indicated $P<0.05$ and a significant difference; and through histological examination, in the traditional Chinese medicine group using the compound preparation for neuranagenesis of the present invention, densely regenerated nerve fibers and thick myelin sheath could be seen, which was obviously better than in the blank control group, and statistical analysis indicated P<0.05 and a significant difference.

The results indicate that: the compound preparation for neuranagenesis of the present invention can promote regeneration, myelination and functional recovery of the injured sciatic nerves in rats.

Example 4: Study on a Protective Effect of the Compound Preparation for Neuranagenesis for Ischemic Brain Injury in Rats Materials and methods: 60 SD rats were randomly divided into 5 groups: low-dose, medium-dose and high-dose groups of the oral liquid of the compound preparation for neuranagenesis, a Huatuo Zaizao pill group (positive control) and an ischemic group (negative control). The low-dose, medium-dose and high-dose groups of traditional Chinese medicine were administered at a dose of 0.9 g/kg, 1.8 g/kg and 3.6 g/kg respectively; the Huatuo Zaizao pill group was administered at a dose of 1.44 g/kg; and the ischemic control group was given with double distilled water at an equivalent volume. Neurological function scoring criteria (*Methodology of Modern Pharmacological Testing* (*Second Volume*)) (notes: scoring criteria: with a full score of 11, a higher score indicates a more severe animal behavior disorder); and determination of SOD activity and MDA content in serum, determination of infarction volume, observation of pathological tissues, observation of ultrastructures and statistical treatment of data were performed.

Results: (1) in the high-dose group of traditional Chinese medicine and the Huatuo Zaizao pill group, the scores of neurological functions in rats at 24 h, 48 h, and 72 h were significantly decreased (P<0.05 and 0.01).

(2) In comparison with the ischemic group, in the medium-dose group and high-dose group of traditional Chinese medicine and the Huatuo Zaizao pill group, the infarction volumes were significantly reduced (P<0.05 and 0.01).

(3) In comparison with the ischemic group, in the medium-dose group and high-dose group of traditional Chinese medicine and the Huatuo Zaizao pill group, the SOD activity was significantly increased, and the MDA content was significantly decreased (P<0.05 and 0.01).

The results indicate that: the oral liquid of the compound preparation for neuranagenesis can improve recovery of the neurological functions causing cerebral ischemia in rats, with a dose-effect relationship; and it can obviously improve the SOD activity and MDA level, and has a good protective effect for nerve injuries.

Described above are just preferred embodiments of the present invention, which are not intended to limit the present invention; and on this basis, partial variations of the formula and process therein should all be included in the scope of the present invention.

What is claimed is:

1. A compound preparation for neuranagenesis, wherein the compound preparation comprises the raw medicinal materials in parts by weight:

10-20 parts of raw *Astragali radix*, 10-20 parts of Rehmanniae *Radix praeparata*, 10-20 parts of *Achyranthes bidentata*, 6-15 parts of *Jujubae fructus*, 6-15 parts of *Lycii fructus*, 6-15 parts of parched *Ziziphi spinosae semen*, 6-12 parts of *Angelicae sinensis radix*, 3-9 parts of *Carthami flos*, 6-15 parts of *Poria*, 6-15 parts of parched *Atractylodis macrocephalae rhizoma* and 10-20 parts of *Zaocys*, and the dosage form of the compound preparation for neuranagenesis comprises oral liquid prepared by:
  soaking the raw materials in deionized water at 25° C. for 120 min;
  performing water extraction, and decocting at 100° C. for 20 min;
  taking the decoction and allowing same to stand at 4° C. for 12 h under sterile conditions, performing filtration and concentration, and adding benzoic acid or sodium benzoate; and
  performing filling and sterilization to obtain the oral liquid.

2. The compound preparation for neuranagenesis according to claim 1, wherein the compound preparation comprises the raw medicinal materials in parts by weight:
  15 parts of raw *Astragali radix*, 15 parts of Rehmanniae *Radix praeparata*, 15 parts of *Achyranthes bidentata*, 10 parts of *Jujubae fructus*, 10 parts of *Lycii fructus*, 10 parts of parched *Ziziphi spinosae semen*, 6 parts of *Angelicae sinensis radix*, 3 parts of *Carthami flos*, 10 parts of *Poria*, 10 parts of parched *Atractylodis macrocephalae rhizoma* and 15 parts of *Zaocys*.

3. The compound preparation for neuranagenesis according to claim 2, wherein the compound preparation also comprises an effective dose of the formulation components of the compound preparation and pharmaceutically acceptable excipients.

4. A method for preparing the compound preparation for neuranagenesis according to claim 3, wherein when the dosage form of the compound preparation is oral liquid, the preparation method further comprises the following step:
  preparing raw materials in parts by weight: 15 parts of raw *Astragali radix*, 10 parts of *Jujubae fructus*, 15 parts of Rehmanniae *Radix praeparata*, 10 parts of *Lycii fructus*, 15 parts of *Achyranthes bidentata*, 10 parts of parched *Ziziphi spinosae semen*, 6 parts of *Angelicae sinensis radix*, 3 parts of *Carthami flos*, 10 parts of *Poria*, 10 parts of parched *Atractylodis macrocephalae rhizoma* and 15 parts of *Zaocys*, and rinsing the medicinal materials with water to remove impurities.

5. A method for preparing the compound preparation for neuranagenesis according to claim 3, wherein when the dosage form of the compound preparation is granules, the preparation method further comprises the following step:
  preparing raw materials in parts by weight: 15 parts of raw *Astragali radix*, 10 parts of *Jujubae fructus*, 15 parts of Rehmanniae *Radix praeparata*, 10 parts of *Lycii fructus*, 15 parts of *Achyranthes bidentata*, 10 parts of parched *Ziziphi spinosae semen*, 6 parts of *Angelicae sinensis radix*, 3 parts of *Carthami flos*, 10 parts of *Poria*, 10 parts of parched *Atractylodis macrocephalae rhizoma* and 15 parts of *Zaocys*, and rinsing the medicinal materials with water to remove impurities.

6. A method of treating nerve damage diseases comprising administering a therapeutically effective amount of the compound preparation for neuranagenesis according to claim 1.

7. A compound preparation for neuranagenesis, wherein the compound preparation comprises the raw medicinal materials in granules:
  15 parts of raw *Astragali radix*, 10 parts of *Jujubae fructus*, 15 parts of Rehmanniae *Radix praeparata*, 10 parts of *Lycii fructus*, 15 parts of *Achyranthes bidentata*, 10 parts of parched *Ziziphi spinosae semen*, 6 parts of *Angelicae sinensis radix*, 3 parts of *Carthami flos*, 10 parts of *Poria*, 10 parts of parched *Atractylodis*

*macrocephalae rhizoma* and 15 parts of *Zaocys*, and rinsing the medicinal materials with water to remove impurities, and the dosage form of the compound preparation for neuranagenesis comprises granules prepared by:

soaking the raw materials in deionized water at 25° C. for 120 min;

performing water extraction, and decocting at 100° ° C. for 20 min;

taking the decoction and allowing same to stand at 4° C. for 12 h under sterile conditions, performing filtration and concentration, and adding benzoic acid or sodium benzoate; and performing drying, granulation, filling and sterilization to obtain the granules.

* * * * *